United States Patent [19]

Phelps et al.

[11] Patent Number: 5,429,137
[45] Date of Patent: Jul. 4, 1995

[54] ACOUSTIC SCAN CONVERSION METHOD AND APPARATUS FOR VELOCITY FLOW

[75] Inventors: Robert N. Phelps, Issaquah; Zoran B. Banjanin, Renton; Jin Kim, Issaquah, all of Wash.

[73] Assignee: Siemens Medical Systems, Inc., Iselin, N.J.

[21] Appl. No.: 253,632

[22] Filed: Jun. 3, 1994

[51] Int. Cl.⁶ .............................................. A61B 8/06
[52] U.S. Cl. .............................................. 128/661.09
[58] Field of Search .......... 128/660.05, 661.08–661.10; 73/861.25

[56] References Cited

U.S. PATENT DOCUMENTS

| | | | |
|---|---|---|---|
| 4,430,514 | 2/1984 | Bofa et al. | 128/661.09 |
| 4,850,364 | 7/1989 | Leavitt | 128/661.09 |
| 4,896,674 | 1/1990 | Seo | 128/661.09 |
| 5,058,594 | 10/1991 | Lazenby | 128/661.09 |
| 5,127,409 | 7/1992 | Daigle | 128/661.09 X |
| 5,188,113 | 2/1993 | Sato et al. | 128/661.09 |
| 5,282,471 | 2/1994 | Sato | 128/661.09 |
| 5,291,892 | 3/1994 | O'Donnell | 128/661.09 |

*Primary Examiner*—Francis Jaworski

[57] ABSTRACT

An ultrasound pulsed Doppler system detects Doppler-shifted acoustic pulses reflected from moving material in a body and received by a transducer, and displays the velocity field of the material on a screen in a color flow format together with the black-and-white display of the ultrasound B-mode of the body. The system detects the average velocity of the material at a plurality of localized sample regions in the body by determining the complex correlation function for pairs of reflected signals from each sample region that are received by the transducer, where the complex phase of the correlation function is proportional to the velocity of the material, projected along the ray from the sample region to the transducer. The display constitutes an array of pixels, and the system determines a value at each pixel that represents the velocity for the material at the location imaged by the pixel. These velocity values are determined by selecting, for each pixel, a plurality of sample regions having images neighboring the pixel, and interpolating separately the real and imaginary parts of the complex correlation value from these sample regions. These interpolated complex correlation function values are used to determine the velocity value for the pixel. The interpolation is carried out using a 2×4 kernel, with 2-point interpolation along the dimension of the ray and 4-point interpolation along the perpendicular azimuthal dimension. In a further improvement, the system also displays the flow turbulence field in a color flow format by determining the average power in the reflected signals from each sample region, interpolating these values to obtain a pixel power value, and using this value and the magnitude of the complex correlation function value to obtain a turbulence estimate value.

23 Claims, 4 Drawing Sheets

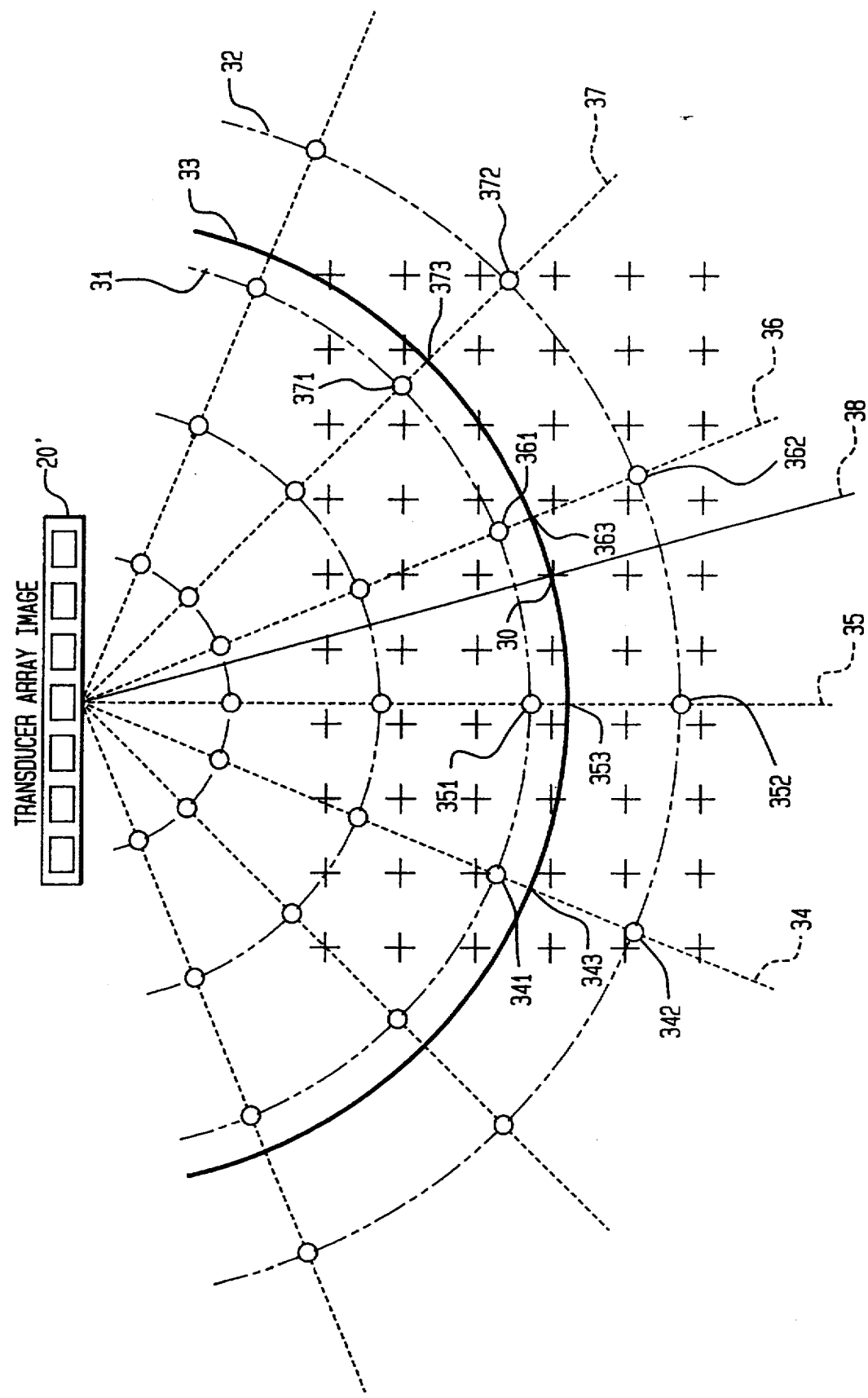

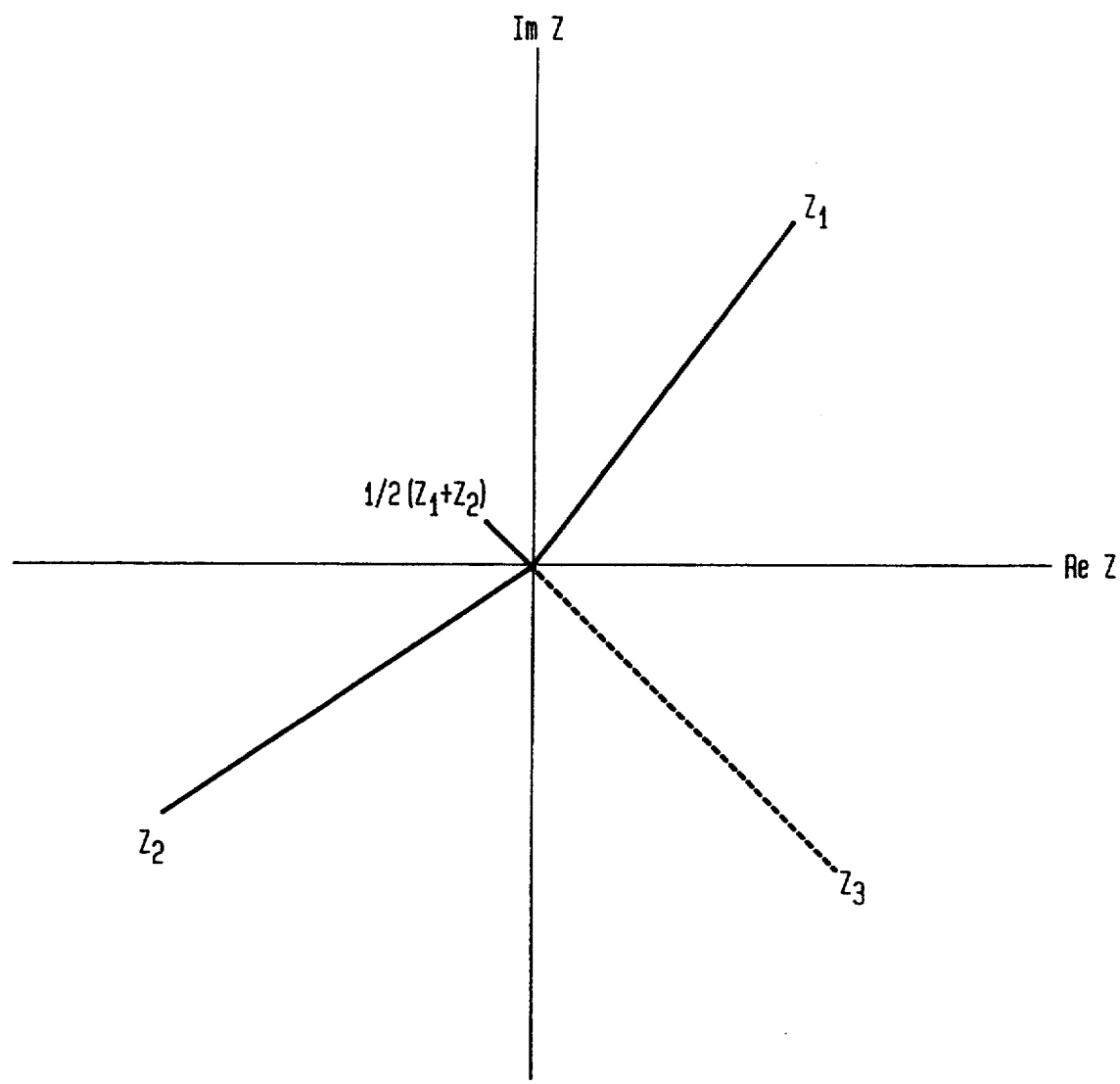

ACOUSTIC SCAN CONVERSION METHOD AND APPARATUS FOR VELOCITY FLOW

BACKGROUND OF THE INVENTION

1. Field of the Invention

This invention relates generally to systems and techniques for displaying electronically images generated from acoustic data. More particularly, the invention is related to means and methods for displaying medical ultrasound images that contain color flow information.

2. Description of the Background Art

Diagnostic ultrasound techniques currently utilize ultrasound to obtain information about the nature and structure of tissues and organs of the human body. This technique has become widely accepted in medicine, partly because it allows a physician to obtain pictorial cross sections of various parts of the body in a noninvasive way, and in some medical specialties, such as obstetrics, ultrasound techniques have virtually supplanted all other imaging methods.

Medical diagnostic ultrasound systems generally yield information concerning structures within the body of a patient by transmitting sound waves of very high frequency, typically on the order of several megahertz, from a transducer into the patient's body and analyzing the echoes reflected from these structures that are detected by the transducer. The transducer operates both as the transmitter and the receiver of the acoustic waves. The information obtained from these echoes can be displayed and studied in several ways, referred to as "modes". The display of information is often on a cathode ray tube (CRT) screen in real time, during the actual examination of the patient.

For example, the A-mode ("Amplitude") display is a plot of the amplitude of the reflected signals as a function of time. The delay time between a transmitted sound wave pulse and a received echo pulse determines the distance from the transducer to the reflecting structure. Furthermore, the acoustic pulses may be focused into a beam along a given direction. This focusing is preferably achieved by utilizing a phased array of transducers, rather than a single transducer. This method allows the user to steer the acoustic beam and adjust the focus dynamically in real time. Therefore, the direction of propagation of the stimulus and echo signals is also determined, and the A-mode display provides information about the location of the reflecting structures along a beam line.

A clearer picture of the geometry of the reflecting structures is provided by the B-scan ("Brightness") display, which represents the amplitude of the reflected signals from a given direction as the brightness of the line along a CRT trace. The distance along the trace is proportional to the distance from the transducer to the reflecting location. By scanning a focused beam of transmitted signals across a sector under examination and simultaneously sweeping the CRT trace in a direction perpendicular to the trace axis ("B-mode"), the resulting display shows reflecting interfaces along a collection of beam lines in a plane section through the body. Thus, the B-mode display comprises a two-dimensional image of a cross section of the structure being studied. With presently available technology these images can be generated and displayed in a real-time mode during the examination of a patient. Thus the B-mode technique is a very useful tool in a clinical environment.

The foregoing B-mode method produces images that may include a direct view of some tissue motion, such as heart wall movement. However the resolution limits of the ultrasound technique imply that smaller structures cannot be studied by this method. This limitation can be significant in some applications, such as cardiac imaging, for example, where important structural features may be too small to be imaged by the B-mode ultrasound method. In such applications it is desirable to obtain information regarding blood flow through the structure, because variations in the velocity of blood flow can reflect diagnostically important anatomical characteristics and abnormalities. For example, vascular obstruction may manifest itself through abnormally high blood flow velocity.

The color flow imaging method is an improvement on the B-mode technique that is designed to include information about blood flow in the ultrasound scan images. This method is described in U.S. Pat. No. 4,800,891, issued Jan. 31, 1989 (Kim), assigned to the assignee of the present invention. The technique involves the measurement of the Doppler shift of acoustic signals reflected from moving targets, such as flowing blood. The Doppler shift in the reflected sound wave frequency is proportional to the projection of the blood flow velocity along the beam axis between the transducer array and the sample point in the blood flow where the reflection originates. The reflected signal therefore carries information about this projected flow velocity. In the color flow imaging method, the projected velocity component is represented as a certain color representing the direction of the flow, and the color intensity varies directly with the magnitude of the blood velocity.

The color flow technique is implemented together with the gray-scale B-mode technique described above by using the pulsed Doppler method. The acoustic stimuli are a train of pulses focused along a beam ray into the body, and this ray direction is swept through the sector under examination. The position of the axis and the arrival time of the reflected pulses at the transducer determine the location of each reflecting sample. In addition, the frequency shift of each reflected pulse determines the velocity projection along the beam ray of the reflecting sample. For each such reflecting sample in the flow pattern, a spot having a color representative of the blood flow velocity is superimposed upon the above-described B-mode image. The composite image thus comprises the gray-scale B-mode image showing the geometry of various structures, together with colored areas within these structures indicating blood flow.

These real-time image-forming techniques generally require a device, termed a "scan converter", for converting the information contained in the reflected acoustic signals into a form suitable for display on a CRT television-type screen. The scan converter is a memory into which information is written in a format corresponding to the acoustic signals received by the transducer, and from which this information is read in a format suitable for CRT display, such as a standard television raster pattern. While the early scan converters were analog devices, digital scan converters (DSC) have been found to be advantageous for medical ultrasound applications. DSC technology has been reviewed in an article by J. Ophir and N. F. Maklad, "Digital Scan Converters in Diagnostic Ultrasound Imaging", published in *Proceedings Of the IEEE*, Vol. 67, No. 4 (April, 1979).

The DSC transforms the coordinates indicating the location of the acoustic reflection points into corresponding positions on the CRT display screen. Acoustic data are typically gathered by scanning the beam rays extending from the transducer array through a sequence of angles traversing the sector of the body under examination. In a given ray the reflected signals are labeled by the distance along the ray from the transducer to the point of reflection. The locations of the reflecting samples are thus specified in polar coordinates in the plane of the sector. However in a standard television display the location of image pixels on the screen is specified in terms of the usual Cartesian x-y coordinates. In the standard display system the DSC carries out a mapping of the acoustic data from polar to Cartesian coordinates.

In addition, the DSC serves as a buffer to compensate for the mismatch between the rate at which data are collected by the acoustic sampling system and the rate at which they can be exhibited by the video display. This function is described in U.S. Pat. No. 4,449,199, issued May 15, 1984 (Daigle).

The coordinate transformation by the DSC typically produces a number of undesirable artifacts in the resulting image, since only a finite number of pixels and polar data sample locations can be processed, and the display at most pixel locations must be interpolated from neighboring polar data sample locations. The interpolation is normally limited to bilinear interpolation between nearest neighbor sampling points. These artifacts can include a blocky appearance of structures, oversampling of some data, and the well-known Moiré artifact. An article by M. H. Lee, J. H. Kim and S. B. Park, "Analysis of a Scan Conversion Algorithm for a Real-Time Sector Scanner", published in *IEEE Transactions on Medical Imaging*, Vol. MI-5, No. 2 (June 1986) reviews many of these problems in the gray-scale B-mode context, along with some of the solutions that have been proposed.

The previously known interpolation techniques for scan converters present further problems when they are used in color flow imaging systems. The images require interpolation of data representing flow velocity as a function of position, as well as the locations of solid structures. According to the conventionally preferred methods as described in Kim, supra, the actual flow velocity data are contained in estimates of the correlation value between pairs of acoustic pulses reflected from the sample region. The correlation value is preferably the first lag autocorrelation, although in principle other correlations can be used. The first lag autocorrelation is represented typically by a complex number, in which the complex phase is proportional to the velocity of the sample. In the conventional method of scan conversion, the magnitude and phase of the first lag autocorrelation is interpolated between sampling points to generate pixel values for representing the flow velocity. Since these data are contained in reflected pulses, the magnitude of the measurable velocity is limited by the pulse rate frequency in accordance with the Nyquist sampling theorem. This limitation is the well-known "aliasing" phenomenon. In regions of large flow velocity, conventional methods can produce images where the flow velocity appears to suddenly reverse direction as a result of this aliasing problem. Furthermore, in regions where the flow velocity gradient is large, such as in the neighborhood of walls, the interpolating process can produce images with artificially irregular flow, again partly due to aliasing of the velocity data, as well as the inherent numerical inaccuracies of the interpolation itself.

SUMMARY OF THE INVENTION

The present invention is a digital scan conversion system and technique for providing improved color flow images. The images are produced by interpolating the first lag autocorrelation that determines the flow velocity. The system interpolates separately both the real and imaginary parts of these complex numbers, and thus provides an improved representation of the complex phase information in the signals. In addition, the system also interpolates separately the magnitude of the first lag autocorrelation and the squared amplitude of the reflected signal pulses, which is proportional to the reflected signal power. These latter quantities are utilized by the system to compute the variance in the fluctuations in flow velocity, which provides a measure of the turbulence in the flow. The interpolation itself can use a larger interpolation kernel than that used in the conventional linear interpolation schemes. At a given pixel, the interpolation over neighboring sampling points may be linear, cubic, or higher degree in both the radial direction and also in the azimuthal (lateral) direction. In one preferred embodiment of the invention, the interpolation is linear ("two-point") in the radial direction, and cubic ("four-point") interpolation in the azimuthal direction.

Accordingly, it is an object of this invention to provide a scan conversion system for medical ultrasound color flow imaging data that overcomes the artifact problems that arise from the interpolation of sampling data to generate pixel values of the desired image. In particular, the present invention is directed toward elimination of blockiness of the images, oversampling of the data, dark spots and abrupt color changes from aliasing problems, and the Moiré artifacts.

It is also an object of the invention to provide a scan conversion system for medical ultrasound color flow imaging that generates pixel data from sampling data by utilizing interpolation kernels that can be larger than the linear interpolation kernels of the conventional systems.

A further object of the invention is to provide a scan conversion system for medical ultrasound color flow imaging that preserves the complex phase information of the sampling data in generating the pixel data that are displayed by the system to represent fluid flow velocity, such as blood flow.

Yet another object of the invention is to provide a scan conversion system for medical ultrasound color flow imaging that preserves the complex phase information of the sampling data in generating the pixel data that are displayed by the system to represent turbulence of fluid flow, such as blood flow turbulence.

These and other objects, features and advantages of the invention will be further understood by examining the drawings together with the detailed description of the invention as follows.

BRIEF DESCRIPTION OF THE DRAWINGS

FIG. 3 is a diagram of a portion of an ultrasound image display screen showing the location of an array of pixels indicated by crosses, and showing also an overlay of the image locations corresponding to data sampling points indicated by circles and the reference location of the transducer array image.

FIG. 5 is a sketch of the complex z-plane with a plot of two complex first lag autocorrelation values $z_1$ and $z_2$ and their two-point interpolation value, $z_3$, calculated by interpolating their magnitudes and phases, and also their two-point interpolation value $\frac{1}{2}(z_1+z_2)$, calculated according to the present method.

DETAILED DESCRIPTION OF THE PREFERRED EMBODIMENTS

Figure 2:
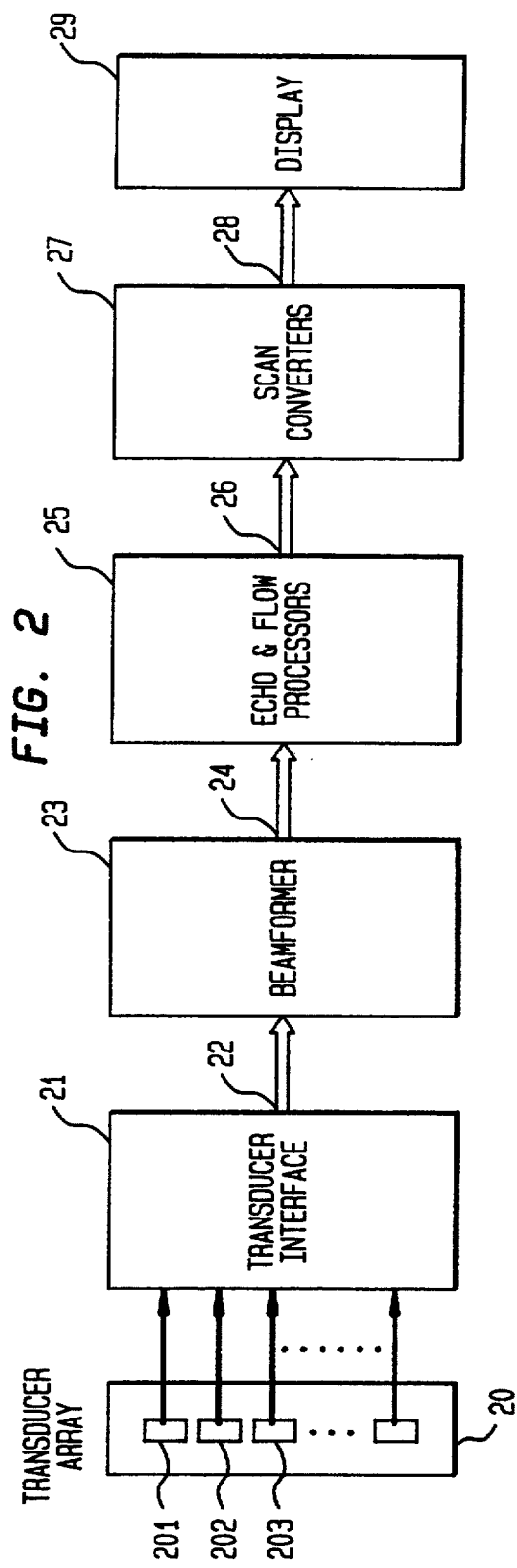
FIG. 2 is a general schematic block diagram of an ultrasound imaging system indicating the flow of signal data through the system and the relationship of the scan converter to the other parts of the system.

FIG. 2 is a schematic block diagram of a typical ultrasonic color flow diagnostic system that incorporates the scan converter of the present invention, showing the flow of signals that are processed by the scan converter. A scan probe 20 is placed in contact with the body of the patient. This probe contains an array of transducers elements 201, 202, 203, . . . that transmit and receive ultrasound signals to and from the body. This array is designed to focus the ultrasound signals to a localized sample region within the body. While this focusing can be achieved in other ways, such as providing a transducer with a shaped surface or an acoustic lens, it is preferable to utilize an array to enable the system to focus the beam dynamically in real time. These transducers generate a sequence of acoustic pulses that propagate into the body and are reflected from internal structures. The reflected pulses are received by the transducers, and the received signals are analyzed to obtain information about the reflecting anatomical features.

The transducers elements 201, 202, 203, . . . form a phased array which are controlled and synchronized so that the broadcast pulses and received signals are dynamically focused along a beam ray in a specific direction from the center of the transducer array into the body. The control and synchronization of these transducers is carded out by the transducer interface 21, which sends the broadcast pulses to the transducer array and receives the plurality of signals from the array. For diagrammatic simplicity the timing and control circuits are omitted from FIG. 2. The plurality of received signals are conveyed through data channel 22 to a beamformer 23, which combines these signals coherently to achieve this focusing effect.

For each transmitted ultrasound pulse into the body along a given beam ray, the beamformer produces a sequence of echo signals from the reflecting structures located along the ray at various depths. These signals are passed through data channel 24 to the echo and flow processor circuits, indicated as block 25 in FIG. 2. The echo and flow processors analyze the sequence of reflected signals generated by the beamformer to determine the location and velocity of the reflecting structures. This analysis is carded out over the entire echo signal for each initial ultrasound pulse. For each portion of the echo signal, the location of the reflecting structure is determined by the direction of the beam ray and the delay time relative to the initial pulse. This determination is used to generate a brightness signal, according to the usual B-mode technique.

A similar echo signal portion is also analyzed to determine the Doppler effect produced by the velocity of the reflecting structure. This determination is preferably carried out for a sequence of pulses and echoes, and the results are statistically analyzed to calculate the average velocity of the reflecting structure and the statistical variance of the velocity. The echo and flow processors 25 therefore generate a plurality of signals for each reflecting sample along the beam ray, indicating the location of the sample point, the magnitude of the reflection, the magnitude of the velocity at the sample point, and the statistical variance of this velocity. The echo and flow processors 25 generate a stream of signals representing these data at various sample points along the beam ray. By sweeping the direction of the beam ray through a sequence of angles, data are collected and processed by the echo and flow processors 25 for each sample point in the scanning plane sector. This data handling technique is similar to the usual B-mode method, except that the data includes color flow velocity data along with the normal echo B-mode data.

The plurality of data signals passes through data channel 26 to the scan converter 27, which converts these signals into a format suitable for CRT display. Typically this display format is a standard television raster pattern. The scan converter 27 utilizes the signals from the data channel 26 to generate display signal values for each pixel in the raster pattern. These display signal values include the color flow velocity data described above, along with the normal B-mode data. The pixel data are conveyed through data channel 28 to the display subsystem 29, which contains a color TV monitor but may also include a color printer, camera, or other color display devices. Various schemes for displaying color flow velocity data can be utilized in this display device, such as the methods described in U.S. Pat. No. 4,641,668, issued Feb. 10, 1987 (Namekawa), or U.S. Pat. No. 4,768,515, issued Sep. 6, 1988 (Namekawa). Preferably the normal B-mode data are displayed in the usual black and white manner, with the color flow data overlaid on the black and white image.

The color flow signals that are generated by the echo and flow processors 25 and processed by the scan converter 27 are preferably the first lag autocorrelation for pairs of received echo signals, and statistics for ensembles of the first lag autocorrelation. One technique for generating these signals is the autocorrelation method, partly described in U.S. Pat. No. 4,573,477, issued Mar. 4, 1986 (Namekawa); the method is also discussed in the article by C. Kasai, K. Namekawa, A. Koyano and R. Omoto, "Real-Time Two-Dimensional Doppler Flow Mapping Using Auto-Correlation", published in *Acoustical Imaging*, Volume 13, edited by M. Kaveh, R. K. Mueller, and J. F. Greenleaf, published by Plenum Press, New York 1984, pp. 447–460, and the article by C. Kasai, K. Namekawa, A. Koyano and R. Omoto, "Real-Time Two-Dimensional Blood Flow Imaging Using an Autocorrelation Technique", published in *IEEE Transactions on Sonics and Ultrasonics*, Volume SU-32, No. 3, May 1985, pp. 458–464.

Figure 4:
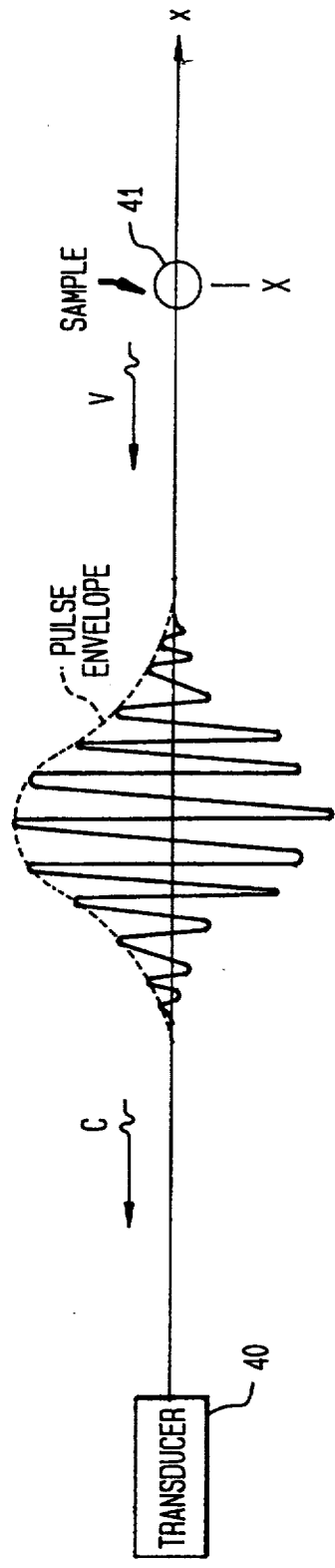
FIG. 4 is a schematic diagram of an idealized reflected ultrasound signal pulse traveling from a moving reflecting sample toward a transducer receiver.

In the autocorrelation technique, the first two moments of the Doppler spectrum are calculated from estimates of the first lag autocorrelation as it is described by R. J. Doviak and D. S. Zmic in "Doppler Radar and Weather Observations", published by Academic Press, 1984. The operation of the Doppler signal portion of the ultrasound system can be described by considering the reflection of a train of ultrasonic signal pulses from a single moving sample as illustrated schematically in FIG. 4. This figure shows an emitting and receiving transducer 40 at the end of a beam ray which is taken to be the x-axis. The origin is defined as the location of the transducer. An ultrasonic pulse having a frequency $f_0$ is emitted by this transducer and propagates along the ray toward the reflecting sample structure 41, which is moving in the negative x direction toward the transducer with a speed denoted as v. The initial pulse reaches the sample at a range gate located at the distance X from the transducer and is reflected back to transducer 40. The transducer emits a sequence of subsequent pulses at time delays that are integer multiples of the Pulse Repetition Time, T; that is, the transducer emits a second pulse at a time delay T after the first pulse, a third pulse at a time delay 2T after the first pulse, . . . , a (k+1)th pulse at a time delay kT after the first pulse, where k=0, 1, 2, 3, . . . , etc. The Pulse Repetition Frequency (PRF) of the emitted pulses is 1/T.

The reflected signals are received by the transducer 40, or more specifically, an array 20 of transducers, and processed by a beamformer 23, as described previously. The flow processors 25 demodulate the received signals by the quadrature method. These signals are electronically multiplied by the signals $2\cos 2\pi f_0 t$ and $2\sin 2\pi f_0 t$ derived from the oscillator that generates the emitted signal pulses, and the high frequency components of the product signals are then filtered out to produce the demodulated quadrature signals. The carrier frequency of the reflected signals is shifted relative to the frequency $f_0$, and the frequency difference is the Doppler shift:

$$f_d = f - f_0 \approx f_0 \cdot \frac{2v}{c}. \quad (1)$$

Typically c is approximately 1,540 meters per second, while the maximum value of blood flow velocity is normally several meters per second, and therefore fd is very small compared to $f_0$.

At the input of the autocorrelator of echo and flow processor 25 there is a sequence of complex signal samples s(kT) produced by each and every sample volume selected by the range gate. These samples are separated by the Pulse Repetition Time (PRT) and they consist of a signal part $a_k e^{j2\pi f_d kT}$ and white noise part $n_k$.

$$s(kT) = a_k e^{j2\pi f_d kT} + n_k, \; k=0,1,\ldots,M-1, \quad (2)$$

where j represents the square root of −1, and M is number of transmitted pulses along a given beam ray, which is equal to the ensemble size. The spectrum of $a_k$ is centered about the zero frequency, whereas the spectrum of s(kT) is centered on the Doppler frequency $f_d$. Both $n_k$ and $a_k$ are zero-mean Gaussian processes (i.e., their average amplitude is zero), but $a_k$ is narrowband compared to the receiver bandwidth. Finally, the flow processors 25 determine the first lag autocorrelation for R(T) for the received complex signals s(kT) as $$R(T) = \frac{1}{M} \sum_{k=0}^{M-2} s^*(kT)s((k+1)T) = D(T) + jN(T), \quad (3)$$

where D(T) and N(T) are real and imaginary parts of the first lag autocorrelation R(T). We can express the first lag autocorrelation R(T) in terms of the Doppler frequency $f_d$ as $$R(T) = e^{j2\pi f_d T} \int_{-1/2T}^{1/2T} S(f) e^{j2\pi (f-f_d)T} df, \quad (4)$$

where S(f) is the power spectrum density of the received signal s(kT). If the spectrum S(f) is symmetric with respect to $f_d$, the imaginary part of the integral is zero and the argument of R(T) gives the frequency $f_d$, i.e., $$f_d = \frac{1}{2\pi T} \arg(R(T)) = \frac{1}{2\pi} \tan^{-1}\left(\frac{N}{D}\right). \quad (5)$$

Using equations (1) and (5) the value of the flow velocity can be calculated as the phase of R(T) divided by a constant of proportionality:

$$v = \frac{c}{4\pi f_0 T} \tan^{-1}\frac{N}{D}. \quad (6)$$

The magnitude of the first lag autocorrelation is $$|R(T)| = \sqrt{D(T)^2 + N(T)^2}, \quad (7)$$

and the power or the zero lag autocorrelation is $$P = R(0) = \frac{1}{M} \sum_{k=0}^{M-1} |s(kT)|^2. \quad (8)$$

These quantities are used to determine the variance of the velocity:

$$\sigma^2 \approx K\left(1 - \frac{|R(T)|}{P}\right), \quad (9)$$

where K is a constant. For steady laminar flow the quantities $|R(T)|$ and P are expected to differ only by a small amount whereas for turbulent flow these quantities differ significantly. Therefore the variance may be a measure of the turbulence in the flow. The variance is the second moment of the deviation of the flow velocity from its average value weighted by the power spectrum, as discussed in the articles by Kasai et al., cited above.

Since the arctangent function is multi-valued, it is necessary to choose a branch of this function in calculating its values, whether by means of an algorithm, a look-up table, or any other method. In order to implement the autocorrelation method, typically the principal branch of this function is chosen such that the calculated values of this function, namely the complex phase angles of the calculated first lag autocorrelation, are limited to values between $-\pi$ and $+\pi$. Equation (6) above indicates that the maximum speed, $v_{max}$, that can be determined by the pulsed Doppler method is obtained by setting the arctangent function to its maximum value, $\pi$:

$$v_{max} = \frac{c}{4f_0 T}. \tag{10}$$

As the actual flow speed increases past this maximum value, the calculated value of the velocity jumps discontinuously to another lower value, located within the principal branch and in the opposite direction. This is the well-known "aliasing" problem for color flow systems.

The foregoing description of the autocorrelation method indicates that the desired information about the flow at a given localized sample region along a given beam ray is obtained from the the first lag autocorrelation and the reflected average power for a pair of signal pulses reflected from this region, and is embodied in three signals determined from these functions, namely N, D, and P, as defined above. In the actual implementation of this method, it is preferable to generate these three signals for an ensemble constituting a plurality of pulse pairs, as described above, and then calculate average values for these pulse-pair signals to increase the signal-to-noise ratio of the results. Typical implementations may collect data for 10 to 20 pulse pairs and then determine the average values for these color flow signals.

In addition, the echo and flow processors 25 also process the normal B-mode magnitude signals for the reflected pulses, along with the previously described color flow signals. The output of the echo and flow processors 25 therefore comprises four signals for each reflecting sample, namely N, D, and P, and the magnitude signal M. This enables the system to provide a display image having an overlay of the color flow distribution along with the geometrical structure provided by the usual B-mode.

The actual reflecting sample structures 41 have a minimum finite size that depends partly on the resolution of the ultrasound technique. The wavelength of ultrasound signals in soft tissue may be typically of the order of a few millimeters, and structures that are substantially smaller than this size cannot be resolved by these ultrasound signals. Therefore, the system divides the field of view for the domain under study into a finite number of sample regions. A "sample point" is a point identifying a sample region, and signals are generated for each of these regions. For a given beam ray, a finite set of sample volumes are defined along that ray, and are selected by a range gate. Similarly, the scan sweep is digitized by defining a finite set of ray directions in the scanned planar sector across the field of view.

FIG. 3 is a simplified diagram, not to scale, of a portion of an image screen for the display device 29. The crosses in FIG. 3 indicate the location on the screen of display pixels, which typically are arranged in a pattern described by rectangular coordinates, such as a standard TV raster pattern. Overlaid on this pattern in FIG. 3 are the image locations corresponding to the locations of the sample regions defined by the system, showing their geometrical relationship to the transducer array. Each circle in FIG. 3 denotes the image of a sample point in the corresponding sample region in the field of view, which is defined typically as the center of the region. The dotted lines in FIG. 3 are the images of the beam rays in the scanned sector, converging toward the apex of the scanned sector image, located at transducer array 20'. It should be noted that it is not necessary that this apex be at the transducer array. The apex of imaging can be above or below the transducer array. The dot-dash circular arcs are the loci of images of constant range locations, including the sample points that are equidistant from the transducer array. The echo and flow processors 25 generate signal values N, D, P, and M for each of the circles shown in FIG. 3, and these signals are conveyed to the scan converter 27 through data channel 26. The scan converter then utilizes these data to generate values of the same variables, N, D, P, and M, for each pixel location. In short, the scan conversion operation is largely a process of converting the field of signal data from polar coordinates to rectangular coordinates, as this Figure illustrates.

By way of example, the scan converter calculates the data values for the pixel 30 by interpolating data values from neighboring sample points 341, 342, 351, 352, 361, 362, 371, and 372, referring still to FIG. 3. This 8-point interpolation is carded out preferably by first interpolation in the radial dimension, followed by second interpolation in the azimuthal dimension. The solid line 38 represents a ray from the scanned sector apex image through the location of pixel 30, and the solid circular arc 33 is the locus of the constant-range circle passing through pixel location 30. The first interpolation in the radial dimension generates data values on this constant-range arc 33 for each of the beam rays 34, 35, 36, 37 on which the sample points are located. For example, on ray 34 a data value is generated corresponding to the intersection point 343 with the arc 33 by interpolating the data values at sample points 341 and 342. This is a linear 2-point interpolation in which the data value for the intersection point 343 is the weighted average of the data values at sample points 342 and 341 and the weights are proportional to the distances between points 341 and 343 and between points 342 and 343, respectively. Similarly, on rays 35, 36, and 37, data values are calculated for points 353, 363, and 373 along the arc 33. Each of these data values is the 2-point interpolation of the data values at sample points 351-352, 361-362, and 371-372, respectively. The result of this first interpolation is to generate four sets of data values corresponding to the points 343, 353, 363, and 373 in FIG. 3. The data values for each of these points are the interpolated values of each of the four variables N, D, P, and M.

The second interpolation utilizes the data values for the four points 343, 353, 363, and 373 to calculate values for the pixel location 30. This calculation is a four-point interpolation in which the weight values are the distances between each of these points and the pixel location 30. This interpolation may be carried out by a variety of well-known methods, such as Newtonian or Lagrangian polynomial interpolation. The resulting interpolated values of N, D, P, and M are conveyed via data channel 28 to the display device 29. The display device utilizes the interpolated values for each pixel location to calculate average velocities and variance values, and converts these values to color display signals. The color display appears on the display screen along with the black-and-white brightness display generated by the interpolated M values.

Figure 1:
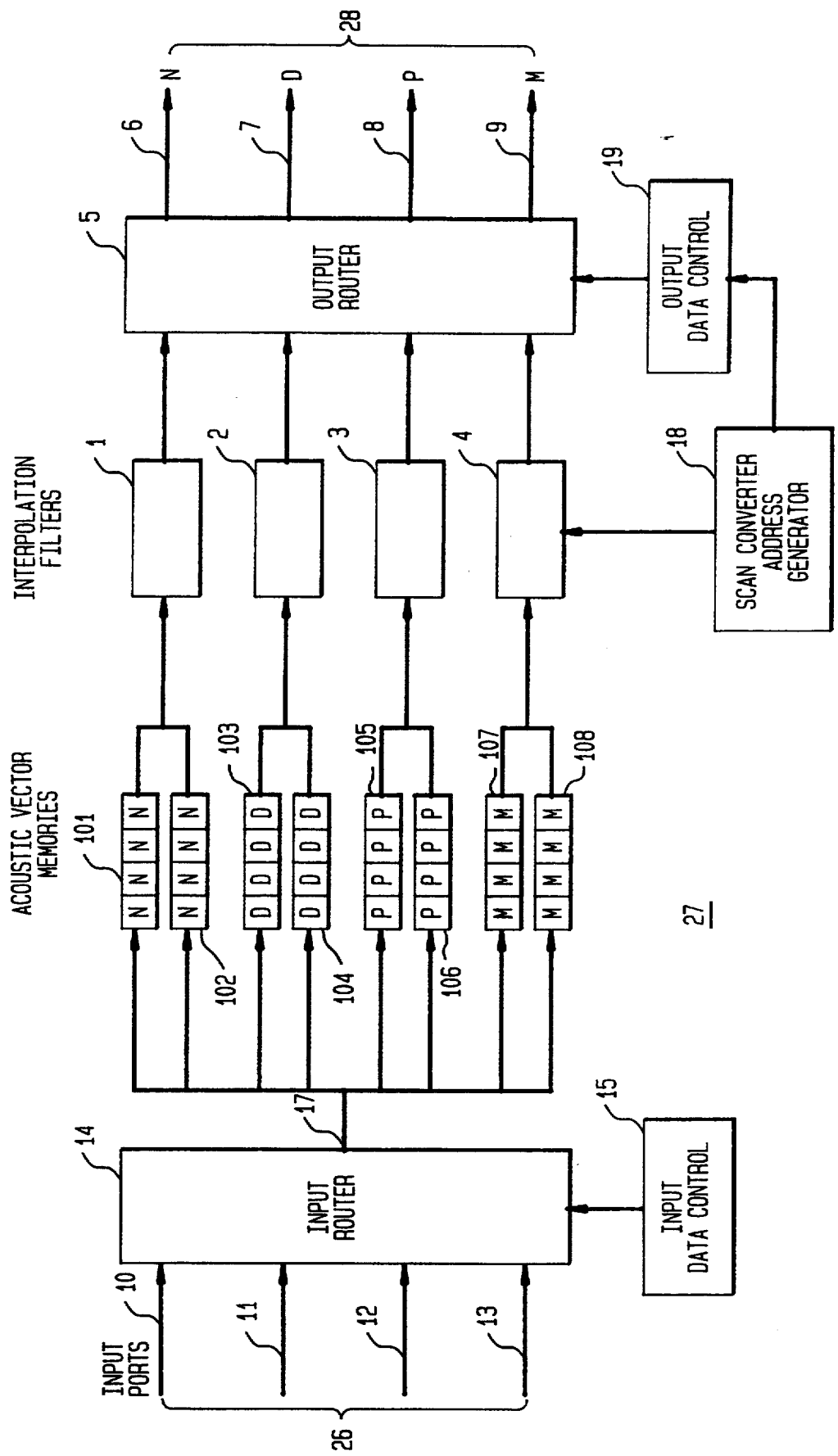
FIG. 1 is a functional block diagram of a scan converter according to the present invention, showing the scan conversion method for converting ultrasound color flow imaging data into pixel data suitable for display.

FIG. 1 shows a functional block diagram of a scan converter that implements the foregoing method. The echo and flow processors 25 generate signal values that are passed to the scan converter 27 through data channel 26 that is constituted of a plurality of ports. In the illustrated implementation, ports 10, 11, 12, and 13 carry this input data. Preferably these ports can be dynamically programmed to carry any one of the four data types generated by the echo and flow processors 25, but the ports are synchronized in their operation so that all of the data signals for neighboring sample points that are required to carry out the interpolation calculations are provided at the proper time. One version of the implementation includes an image memory, not shown in FIG. 1, that receives data from the echo and flow processors and stores this data for an entire image. The image memory feeds this data to the scan converter 27 through ports 10–13 in the proper sequence to provide the proper signals for interpolation calculations.

The input ports 10–13 channel the input data to the input router 14 which also receives signals from an input data control unit 15 that label these data. The data are stored in an input data buffer, included in the input router 14. Data for eight sample points are read out from the input router into the acoustic memories 101 through 108. Preferably the input data buffer is operated in a "ping-pong" fashion, in that data are read into one section of the buffer while being simultaneously read out from another section of the buffer. In the case of 2×4 interpolation kernel size, data for eight sample point "N" signals are read into acoustic vector memories 101 and 102. Similarly, the "D" signals for the same eight sample points are read into memories 103 and 104, while the "P" data are read into memories 105 and 106, and the "M" data are read into memories 107 and 108. It should be noted that for different interpolation kernels different numbers of D, N and P data points are written into these memories.

With these data stored in the acoustic vector memories, the scan converter then calculates the interpolated values for each of the pixel locations having these eight sample points as neighboring points. Referring again to FIG. 3, for example, the data for sample points 341, 342, 351, 352, 361, 362, 371, and 372 are read into the acoustic vector memories, and then the interpolated values are calculated for all pixel locations on the circular arc 33 bounded by the rays 35 and 36. The interpolated values are generated by interpolation filters 1–4 shown in FIG. 1. For a given set of eight sample points, pixel location addresses are generated by the scan converter address generator 18, sequentially for each of the pixels in the region bounded by these sample points as defined above. These addresses are conveyed to the interpolation filters 1–4. For each such pixel address, the interpolation filters calculate corresponding weighting coefficients. Using these coefficients these filters then calculate interpolated values for each type of data; that is, filter 1 calculates the interpolated value of N, filter 2 calculates the interpolated value of D, filter 3 calculates the interpolated value of P, and filter 4 calculates the interpolated value of M.

The interpolated values of these variables are transmitted to the output router 5. This output router 5 also receives signals from the scan converter address generator 18 through the output data control unit 19, which generates labels identifying the pixel locations for these data. The output router 5 thus labels the interpolated values according to their pixel addresses. The labeled output signals are transmitted in parallel to the display device 29 through data channel 2–8, which includes separate output ports 6, 7, 8, and 9, as shown in FIG. 1.

The display device 29 utilizes these data to generate the color flow display as previously described.

The interpolation method of the present invention overcomes the drawbacks inherent in previous scan conversion systems. The independent interpolation of the real and imaginary components of the first lag autocorrelation produces a substantial improvement in the resulting display. The interpolated values are more realistic and reliable than the corresponding values obtained by the previous method of interpolating the magnitudes and complex phases of the first lag autocorrelation. A simple illustration of this improved technique is shown in FIG. 5, which is a plot of the complex z-plane with two complex numbers, $z_1$ and $z_2$, representing complex correlation data at two sample points. In this Figure, the dotted line labeled $z_3$ is a plot of the complex number that would result from calculating the average separately for the magnitudes and phase angles of $z_1$ and $z_2$ according to previous methods. The average value using the present method is also plotted, labeled $\frac{1}{2}(z_1+z_2)$. Clearly these two methods of interpolation give drastically different results. The magnitude of the interpolated value using the present method is several times smaller than the magnitude that would be calculated from the previous methods, and the phase angles differ by 180°.

For purposes of interpolating the first lag autocorrelation for signals generated in ultrasound color flow systems, the present method is superior because it presents a more accurate picture of the physical phenomena that are being modeled. This improvement is important in situations where flow regions with large gradients are being studied. FIG. 5 illustrates an example of data interpolation for two sample points having flow velocities in opposite directions. Physically this corresponds to a region having a large shear in the flow field. In the previous method where the magnitudes and angles of the first lag autocorrelations are separately interpolated, an inherent assumption is made that the flow velocity varies smoothly between the two sample points. However in reality a degree of turbulence is expected between the two sample points, especially since the fluids that are studied in medical applications, such as blood, are relatively viscous. With the present method as shown in FIG. 5, the interpolated value of the first lag autocorrelation has a substantially decreased magnitude compared to its value at the sample points, and this produces an increase in the variance $\sigma^2$, calculated according to equation (9), supra. With the interpolated value $z_3$ obtained by the previous interpolation method as illustrated in FIG. 5, this increase would not be reflected in the resulting display.

It is found that in fact the present interpolation system substantially overcomes the artifact problems found in previous systems described above, including the blocky appearance of structures, oversampling of some data, and the Moiré artifact. The aliasing problem is also improved by this method. As FIG. 5 indicates, the velocity value calculated from the interpolated the first lag autocorrelation, $\frac{1}{2}(z_1+z_2)$, is larger than the velocity at either sample point $z_1$ or $z_2$ (i.e. the complex phase of $\frac{1}{2}(z_1+z_2)$ is larger than the phase of $z_1$ or $z_2$). This peculiar result is related to the aliasing phenomenon, since it arises from the discontinuity in the complex argument of z on the negative real axis. However the magnitude of the interpolated value $\frac{1}{2}(z_1+z_2)$ is substantially reduced, and therefore the amplitude of the displayed reflection signal will also be decreased. This reduction helps to mitigate this "aliasing" effect.

The scan conversion method of this invention has been described specifically for a pulsed Doppler system in which flow velocities are detected by the autocorrelation method. The technique is disclosed in the patent to Kim, supra, improves above autocorrelation method by performing additional averaging along a given beam ray. The scan conversion method set forth herein is not limited to the specific flow detection techniques described above, but is applicable generally to pulsed Doppler systems which estimate the first lag autocorrelation between different pulses to determine flow velocities.

The invention also is not limited to the particular 8-point interpolation procedure that is disclosed herein. Obviously one could carry out the first interpolation in the azimuthal dimension and then perform the second interpolation along the radial dimension for the pixel values being calculated. There are also many different ways of interpolating values using 8-point kernels. The results of this scan conversion method can be improved further by enlarging the scope of the interpolation, i.e. by including more sample points in the interpolation kernel. The scan converter can also be made simpler by decreasing the scope of the interpolation, i.e., by including fewer sample points in the interpolation kernel, e.g., 2×2 interpolation.

The foregoing description of the preferred embodiments is set forth to enable persons skilled in the art to which the invention pertains to make and use the invention. It is intended only for purposes of illustration and elucidation, and not for purposes of limitation. Obviously many variations, modifications, and additions may be made to the method and system disclosed above, in addition to those already described, without departing from the spirit and scope of the invention. It is intended rather that the scope of the invention be determined solely by reference to the following claims.

What is claimed is:

1. In a system for representing the velocities of material at a plurality of different locations in a planar section of a body by directing a plurality of acoustic signals into said body and detecting the Doppler-shifted acoustic signals reflected from a plurality of sample regions in said section, and by displaying an image of said section that is defined by an array of pixels, each pixel having a pixel location point in said image, each pixel further having a velocity value representing the velocity of the material at said pixel location point, a method for determining said velocity value for each of said pixels, said method comprising the steps of:

selecting a plurality of said sample regions in said section for determining said pixel velocity value by interpolation of data contained in acoustic signals reflected from said sample regions;

for each of said sample regions, determining the correlation value for a pair of said reflected acoustic signals, such that said correlation value is a complex number with a phase that equals the average velocity of material in said sample region multiplied by a constant of proportionality;

interpolating the real part of said correlation value from said sample regions to determine a real part of the correlation value for said pixel;

interpolating the imaginary part of said correlation value from said sample regions to determine an interpolated imaginary part of the correlation value for said pixel;

determining the phase of said correlation value for said pixel, said correlation value being defined by said real part and said imaginary part; and dividing said phase by said constant of proportionality to determine said pixel velocity value.

2. A method as recited in claim 1, further comprising the step of displaying each of said pixels in a color that is determined by said pixel velocity value.

3. A method as recited in claim 2, further comprising the step of displaying the B-mode obtained by directing a plurality of acoustic signals into said body and detecting the acoustic signals reflected from a plurality of sample regions in said section as an overlay on said image defined by said color pixels.

4. A method as recited in claim 1, wherein said plurality of acoustic signals directed into said body includes a sequence of separate acoustic pulses having a uniform frequency and repetition rate, wherein the step of determining the correlation value for a pair of said reflected acoustic signals comprises the step of determining the correlation value for a successive pair of acoustic pulses reflected from said sample region.

5. A method as recited in claim 4, wherein the step of interpolating the real part of said correlation value from said sample regions includes the further step of determining the average of said real parts of said correlation value for a plurality of successive pairs of said reflected acoustic pulses;

wherein the step of interpolating the imaginary part of said correlation value from said sample regions includes the further step of determining the average of said imaginary parts of said correlation value for a plurality of successive pairs of said reflected acoustic pulses; and wherein the step of determining the phase of said correlation value for said pixel includes the step of determining the phase of the average correlation value for said pixel defined by said averages of said real parts and said imaginary parts.

6. A method as recited in claim 1, wherein said plurality of acoustic signals directed into said body includes a sequence of separate acoustic pulses having a uniform frequency and repetition rate, wherein the step of determining the correlation value for a pair of said reflected acoustic signals comprises the step of determining the correlation value for a pair of reflected acoustic pulses from adjacent sample regions.

7. A method as recited in claim 6, wherein the step of interpolating the real part of said correlation value from said sample regions includes the further step of determining the average of said real parts of said correlation value for a plurality of pairs of said reflected acoustic pulses from adjacent sample regions;

wherein the step of interpolating the imaginary part of said correlation value from said sample regions includes the further step of determining the average of said imaginary parts of said correlation value for a plurality of pairs of said reflected acoustic pulses from adjacent sample regions; and wherein the step of determining the phase of said correlation value for said pixel includes the step of determining the average phase component of the correlation value for said pixel defined by said averages of said real parts and said imaginary parts.

8. A method as recited in claim 1, in a system wherein said acoustic signals are focused along a plurality of beam rays converging to acoustic signal detection means, and wherein each of said sample regions is located on one of said beam rays, said acoustic signal detection means corresponding to an image location and each of said beam rays corresponding to an image ray, wherein the step of selecting a plurality of sample regions in said section comprises the steps of:

selecting a plurality of neighboring image rays passing the closest distance to said pixel location point; and for each of said plurality of image rays, selecting a plurality of neighboring sample regions located on said image ray at distances from said signal detection means image location that are closest to the distance of said pixel location point from said signal detection means image location;

whereby said interpolations steps are carried out by means of an interpolation kernel having coefficients determined by the locations of said selected sample regions and said pixel location point.

9. A method as recited in claim 8, wherein the step of selecting a plurality of image rays comprises the step of selecting the four image rays passing the closest distance to said pixel location point; and wherein the step of selecting a plurality of sample regions on said image ray comprises the step of selecting the two sample regions located at distances from said signal detection means image location that are closest to the distance of said pixel location point from said signal detection means image location;

whereby said interpolation steps are carried out by means of a 2×4 interpolation kernel having coefficients determined by the locations of said selected sample regions and said pixel location point.

10. In a system for representing the velocities and turbulence estimates of material at a plurality of different locations in a planar section of a body by directing a plurality of acoustic signals into said body and detecting the Doppler-shifted acoustic signals reflected from a plurality of sample regions in said section, and by displaying an image of said section that is defined by an array of pixels, each pixel having a pixel location point in said image, each pixel further having a velocity value and a turbulence value representing the velocity and turbulence estimate, respectively, of the material at said pixel location point, a method for determining said velocity value and turbulence value for each of said pixels, said method comprising the steps of:

selecting a plurality of said sample regions in said section for determining said pixel velocity value and turbulence value by interpolation of data contained in acoustic signals reflected from said sample regions;

for each of said sample regions, determining the correlation value for a pair of said reflected acoustic signals, such that said correlation value is a complex number with a phase that equals the average velocity of material in said sample region multiplied by a constant of proportionality;

for each of said sample regions, determining the average power of said reflected acoustic signals;

interpolating the real pan of said correlation value from said sample regions to determine a real part of a correlation value for said pixel;

interpolating the imaginary part of said correlation value from said sample regions to determine an interpolated imaginary part of a correlation value for said pixel;

interpolating the average power of said reflected acoustic signals from said sample regions to determine an interpolated average power for said pixel;

determining the phase of said correlation value for said pixel, said correlation value being defined by said real part and said imaginary part;

dividing said phase by said constant of proportionality to determine said pixel velocity value;

determining the magnitude of said correlation value for said pixel, said correlation value being defined by said real part and said imaginary part; and determining said pixel turbulence value from said magnitude of said correlation value and said interpolated average power for said pixel.

11. A method as recited in claim 10, wherein the step of determining said pixel turbulence value generates a value proportional to the variance defined by the expression:

$$\sigma^2 \cong k\left(1 - \frac{|R|}{P}\right)$$

where $|R|$ represents said magnitude of said correlation value, P represents said interpolated average power for said pixel, and k is a constant.

12. A method as recited in claim 10, further comprising the step of displaying each of said pixels in a color that is determined by said pixel velocity value and turbulence value.

13. A method as recited in claim 12, further comprising the step of displaying the B-mode obtained from said acoustic signals reflected from said sample regions in said section as an overlay on said image defined by said color pixels.

14. A method as recited in claim 10, wherein said plurality of acoustic signals directed into said body includes a sequence of separate acoustic pulses having a uniform frequency and repetition rate, wherein the step of determining the correlation value for a pair of said reflected acoustic signals comprises the step of determining the autocorrelation value for a successive pair of acoustic pulses reflected from said sample region.

15. A method as recited in claim 14, wherein the step of interpolating the real part of said correlation value from said sample regions includes the further step of determining the average of said real parts of said correlation value for a plurality of successive pairs of said reflected acoustic pulses;

wherein the step of interpolating the imaginary part of said correlation value from said sample regions includes the further step of determining the average of said imaginary parts of said correlation value for a plurality of successive pairs of said reflected acoustic pulses;

wherein the step of determining the phase of said correlation value for said pixel includes the step of determining the phase of the average correlation value for said pixel defined by said averages of said real parts and said imaginary parts; and wherein the step of interpolating the average power of said reflected acoustic signals from said sample regions includes the further step of determining the average power for a plurality of successive pairs of said reflected acoustic pulses.

16. A method as recited in claim 10, wherein said plurality of acoustic signals directed into said body includes a sequence of separate acoustic pulses having a uniform frequency and repetition rate, wherein the step of determining the correlation value for a pair of said reflected acoustic signals comprises the step of determining the correlation value for a pair of reflected acoustic pulses from adjacent sample regions.

17. A method as recited in claim 16, wherein the step of interpolating the real part of said correlation value from said sample regions of includes the further step of determining the average of said real pans of said correlation value for a plurality of pairs of said reflected acoustic pulses from adjacent sample regions;

wherein the step of interpolating the imaginary part of said correlation value from said sample regions includes the further step of determining the average of said imaginary pans of said correlation value for a plurality of pairs of said reflected acoustic pulses from adjacent sample regions;

wherein the step of determining the phase of said correlation value for said pixel includes the step of determining the phase of the average correlation value for said pixel defined by said averages of said real pans and said imaginary parts; and wherein the step of interpolating the average power of said reflected acoustic signals from said sample regions includes the further step of determining the average power for a plurality of pairs of said reflected acoustic pulses from adjacent sample regions.

18. A method as recited in claim 10, in a system wherein said acoustic signals are focused along a plurality of beam rays converging to acoustic signal detection means, and wherein each of said sample regions is located on one of said beam rays, said acoustic signal detection means corresponding to an image location and each of said rays corresponding to an image ray, wherein the step of selecting a plurality of sample regions in said section comprises the steps of:

selecting a plurality of neighboring image rays passing the closest distance to said pixel location point; and for each of said plurality of image rays, selecting a plurality of neighboring sample regions located on said image ray at distances from said signal detection means image location that are closest to the distance of said pixel location point from said signal detection means image location;

whereby said interpolation steps are carded out by means of an interpolation kernel having coefficients determined by the locations of said selected sample regions and said pixel location point.

19. A method as recited in claim 18, wherein the step of selecting a plurality of image rays comprises the step of selecting the four image rays passing the closest distance to said pixel location point; and wherein the step of selecting a plurality of sample regions on said image ray comprises the step of selecting the two sample regions located at distances from said signal detection means image location that are closest to the distance of said pixel location point from said signal detection means image location;

whereby said interpolation steps are carded out by means of a 2×4 interpolation kernel having coefficients determined by the locations of said selected sample regions and said pixel location point.

20. Apparatus for receiving a plurality of complex correlation signals having real and imaginary components for a sequence of pairs of acoustic pulses reflected from a plurality of sample regions in a planar section of a body, said complex correlation signals having complex phases that are proportional to the velocity of material in the reflecting sample regions, and for converting said signals into correlation signal values for an array of pixels defining an image of flow of material in said section, said apparatus comprising:

storage memory for receiving and storing a plurality of said correlation signals and for labeling each of said signals with label information describing the location of the sample region that reflected the signal;

control means communicative with said storage memory for selecting, for each of said pixels, correlation signals corresponding to a plurality of sample regions for generating signal values for said pixel;

a first vector memory into which the labeled real components of said selected correlation signal values are stored by said control means;

a second vector memory into which the labeled imaginary components of said selected correlation signal values are stored by said control means;

an address generator for producing address data, for each of said pixels, describing the location of the pixel;

a first interpolation filter communicative with said first vector memory and said address generator for interpolating said real components of said selected correlation signal values, and for determining the coefficients of the interpolation kernel from the location data provided by said address generator and the label information in the contents of said first vector memory, to produce an interpolated real component of a correlation value corresponding to said pixel;

a second interpolation filter communicative with said second vector memory and said address generator for interpolating said imaginary components of said selected correlation signal values, and for determining the coefficients of the interpolation kernel from the location data provided by said address generator and the label information in the contents of said second vector memory, to produce an interpolated imaginary component of a correlation value corresponding to said pixel; and an output router communicative with said address generator and with said first and second interpolation filters, for receiving said real component and said imaginary component of said correlation value corresponding to said pixel, labeling said components with information indicating the location of said pixel, and transmitting said components to a display device.

21. Apparatus as recited in claim 20, further comprising means for receiving a plurality of signals produced by acoustic signals reflected from sample regions in said planar section of said body and converting said signals into signal values for an array of pixels defining an image of reflecting material in said section.

22. Apparatus as recited in claim 20, wherein said control means further comprises:

means for selecting a plurality of neighboring image rays image rays passing the closest distance to the location of said pixel; and for each of said plurality of image rays, means for selecting a plurality of sample regions located on said image ray at distances from the signal detector image location that are closest to the distance of said pixel location from said signal detector image location;

whereby the coefficients of the interpolation kernel of said first and second interpolation filters are determined by the locations of said selected sample regions and said pixel location.

23. Apparatus as recited in claim 20, said apparatus further receiving a plurality of average pulse power signals for said sequence of pairs of acoustic pulses, and for converting said pulse power signals into pulse power signal values for an array of pixels defining an image of flow of material in said section, said apparatus further comprising:

storage memory for receiving and storing a plurality of said pulse power signals and for labeling each of said signals with label information describing the location of the sample region that reflected the signal;

control means communicative with said storage memory for selecting, for each of said pixels, pulse power signals corresponding to a plurality of sample regions for generating pulse power signal values for said pixel;

a third vector memory into which the labeled pulse power signal values are stored by said control means; and a third interpolation filter communicative with said third vector memory and said address generator for interpolating said selected pulse power signal values, and for determining the coefficients of the interpolation kernel from the location data provided by said address generator and the label information in the contents of said third vector memory, to produce an interpolated pulse power signal value corresponding to said pixel;

said output router further being communicative with said third interpolation filters, for receiving said pulse power signal value corresponding to said pixel, labeling said pulse power signal value with information indicating the location of said pixel, and transmitting said pulse power signal value to a display device.

* * * * *